(12) United States Patent
Jenkins

(10) Patent No.: US 8,776,787 B2
(45) Date of Patent: Jul. 15, 2014

(54) ADAPTOR AND BREATHING ASSIST DEVICE USING THE SAME

(75) Inventor: Eddie Dewayne Jenkins, Chattanooga, TN (US)

(73) Assignees: Eddie Dewayne Jenkins, Chattanooga, TN (US); Reta June Standefer, Chattanooga, TN (US)

( * ) Notice: Subject to any disclaimer, the term of this patent is extended or adjusted under 35 U.S.C. 154(b) by 451 days.

(21) Appl. No.: 12/637,540

(22) Filed: Dec. 14, 2009

(65) Prior Publication Data

US 2011/0041843 A1    Feb. 24, 2011

Related U.S. Application Data

(60) Provisional application No. 61/274,711, filed on Aug. 20, 2009.

(51) Int. Cl.
*A61M 16/08* (2006.01)
*A61M 16/16* (2006.01)
*A61M 16/10* (2006.01)

(52) U.S. Cl.
CPC ....... *A61M 16/0808* (2013.01); *A61M 16/1045* (2013.01); *A61M 16/08* (2013.01); *A61M 2016/106* (2013.01)
USPC ............ 128/201.13; 128/205.12; 128/204.13; 128/200.24

(58) Field of Classification Search
CPC . A61M 16/1045; A61M 16/08; A61M 16/16; A61M 16/06; A61M 2230/432; A61M 16/00; A61M 16/1055; A61M 16/105; A61M 16/0666; A61M 16/22; A61M 11/06; A61M 16/1075; A61M 16/0066; A61M 16/0808

USPC ........... 128/201.13, 205.12, 205.27; 116/200, 116/206, 264, 112

See application file for complete search history.

(56) References Cited

U.S. PATENT DOCUMENTS

| | | | |
|---|---|---|---|
| 3,216,413 A | 11/1965 | Mota | |
| 3,454,005 A | 7/1969 | Eubanks et al. | |
| 3,916,891 A | 11/1975 | Freytag et al. | |
| 4,090,513 A * | 5/1978 | Togawa | 128/201.13 |
| 4,200,094 A * | 4/1980 | Gedeon et al. | 128/201.13 |
| 4,360,018 A * | 11/1982 | Choksi | 128/205.12 |
| 4,457,305 A | 7/1984 | Shanks et al. | |
| 4,714,486 A * | 12/1987 | Silverthorn | 96/134 |
| 4,798,676 A * | 1/1989 | Matkovich | 210/767 |
| 4,867,153 A | 9/1989 | Lorenzen et al. | |
| 4,929,259 A * | 5/1990 | Caskey et al. | 210/321.89 |
| 5,022,900 A * | 6/1991 | Bar-Yona et al. | 96/142 |

(Continued)

FOREIGN PATENT DOCUMENTS

WO    WO-2005/047797 A2    5/2005

*Primary Examiner* — Annette Dixon
(74) *Attorney, Agent, or Firm* — Muncy, Geissler, Olds & Lowe, P.C.

(57) ABSTRACT

An adaptor includes a housing and a plurality of blades disposed inside the housing. The adaptor can be utilized with a breathing assist device such as a Continuous Positive Airway Pressure (CPAP) machine. Air flowing through an air flow path defined by the two ends of the housing is delivered for use. The blades within the housing are aligned in a direction parallel to the air flow path. The blades within the housing can be parallel, zigzag or chevron shape and are designed to facilitate condensation of water from the air flowing over the blades. The adaptor will reduce rain-out effect in the breathing device.

19 Claims, 3 Drawing Sheets

(56) References Cited

U.S. PATENT DOCUMENTS

| | | | |
|---|---|---|---|
| 5,035,236 A * | 7/1991 | Kanegaonkar | 128/201.13 |
| 5,038,775 A * | 8/1991 | Maruscak et al. | 128/205.27 |
| 5,101,821 A | 4/1992 | Carie, Jr. | |
| 5,160,511 A * | 11/1992 | Lovelock | 95/52 |
| 5,228,436 A | 7/1993 | Parkin | |
| 5,320,096 A * | 6/1994 | Hans | 128/205.29 |
| 5,349,946 A | 9/1994 | McComb | |
| 5,398,677 A | 3/1995 | Smith | |
| 5,657,750 A * | 8/1997 | Colman et al. | 128/205.12 |
| 5,826,575 A | 10/1998 | Lall | |
| 5,902,520 A * | 5/1999 | Vezzani | 261/84 |
| 6,095,505 A | 8/2000 | Miller | |
| 6,415,788 B1 | 7/2002 | Clawson et al. | |
| 6,606,994 B1 | 8/2003 | Clark | |
| 6,904,911 B2 * | 6/2005 | Gibertoni | 128/201.13 |
| 7,905,937 B2 * | 3/2011 | Nieuwoudt | 55/444 |
| 7,913,640 B2 * | 3/2011 | MacDonald et al. | 116/206 |
| 2006/0144399 A1 | 7/2006 | Davidowski et al. | |
| 2009/0020124 A1 | 1/2009 | Roth et al. | |

* cited by examiner

ADAPTOR AND BREATHING ASSIST DEVICE USING THE SAME

DOMESTIC PRIORITY STATEMENT

This application claims the benefit of U.S. Provisional Application Ser. No. 61/274,711, filed Aug. 20, 2009 in the United States Patent & Trademark Office in the name of Eddie D Jenkins et al, entitled "Rain-Out Guard", the disclosure of which is incorporated herein in its entirety by reference.

BACKGROUND

1. Field of the Disclosure

The present disclosure relates generally to a medical device. More particularly, the present disclosure relates to an adaptor to prevent water condensation in a breathing assist device such as a Continuous Positive Airway Pressure (CPAP) machine.

2. Description of Related Art

A breathing assist device supplies air to a user or patient. Normally, when people breathe, the air becomes humid and sufficiently warm to go into the lungs because the human nasal cavity regulates humidity of the air. However, if a breathing assist device is used by the user/patient, the air or medical gas provided by the breathing assist device alone may be very dry so that it harms the trachea. Alternatively, if the air provided does not go through the human nasal system, the air will be too dry for the respiratory system. Over dryness of the inhaled air may harm the trachea and lung tissue. To resolve this problem, an auxiliary device is utilized to provide sufficient humidity to the air/gas supplied from the breathing assist device.

The auxiliary device or humidifier will add moisture and/or heat to the inhaled air or gas. For example, a commonly used humidifier introduces water vapor into the air or gas to maintain a certain degree of humidity so that the air or gas is sufficiently humid to avoid harming the lung tissues because of over dryness. The water vapor stays in the air to maintain the humidity if the air temperature is maintained within a certain range. However, the humidified air/gas is delivered through tubing. As the air passes through the tubes or other surfaces, its temperature will lower. Once the air sufficiently cools, the water vapor carried in the air will condense. As a result, rain-out will occur which means that water will condense inside the tubes or in the mask of the user/patient.

Rain-out can cause the tubing to rattle as air continues to pass therethrough. This is noisy and disturbing to the user and others nearby. Dripping or puddling of water within the mask is also a discomfort for the user. In fact, if enough water accumulates in the mask or end of the tubing, the rain-out can also cause choking of the user. Even worse, some unwanted bacteria can accumulate in the condensed water which can cause an infection for the patient.

Several solutions to the problem of rain-out have been developed. One of the solutions is using a heating element to heat up the tube. As air goes through the tube, it will not cool down and not condense. However, using heating elements can be costly and causes more design complexity.

Accordingly, it is desirable to provide an apparatus for avoiding water condensation in the breathing assist device. It is further desirable that the apparatus reduces the need to use a separate heating device to remove excess water from the air and thus reduce design complexity and costs.

SUMMARY

An example embodiment of the present invention includes an adaptor, with a housing and a plurality of blades disposed therein. The housing can be a tubular shape and can have two ends defining a path of air flow. The air flowing along the path of air flow is delivered for use by the patient. The shape of the blades within the housing is designed to facilitate water condensation from the air passing over them. The shape can be arranged in a parallel, zigzag, chevron or any desired pattern. The shape of the blades themselves can be in flat shape, curved, wing-shaped or any other desired configuration.

The adaptor has a housing and a plurality of blades as noted above. The plurality of blades can be divided into two sets of blades, a first set and a second set. In one embodiment these two sets of blades have different shapes; however, in another embodiment, these two sets of blades can be the same shape. In addition, the alignments of the two sets of blades are different; for example, the alignment of the two sets of blades are perpendicular to each other in one embodiment.

Another embodiment of the adaptor has three sets of blades inside the housing. In this embodiment, the shapes of the three sets of blades can vary or be the same. Each of the three sets of blades can be different, or a pair of the three can be the same or all blades in each set can be the same. Moreover, the plurality of blades in the adaptor in other embodiments of the present invention can be divided into more than three sets of blades. While the adaptors in these embodiments of the present invention have some different modifications, they share common features and inventive concepts of the present invention.

In another aspect of the present invention, a breathing assist device utilizing the adaptor described above is provided. The breathing assist device includes an adaptor, an air source, a tubing device and a mask. Air is supplied from the air source and goes through the adaptor and the tubing device. A user/patient wearing the mask breathes in air through the mask. This user/patient can be human or non-human such as a dog or other animal being treated by a veterinarian, for example. The breathing assist device further comprises a humidifier to maintain certain humidity in the air in order avoid over dry air. The adaptor disposed in the breathing assist device facilitates condensation of excess water from the air and keeps water from condensing in the tubing device or the mask. As a result, the breathing device utilizing the adaptor will prevent rain-out. Rattling of the tubing, unwanted condensation and chocking of the use/patient can be avoided.

These and other objects of the invention are fulfilled by an adapter used in a breathing assist device. The adaptor comprises a housing having two ends and a plurality of blades disposed in the housing. The blades are aligned in a direction of air flow. A path of air flows through both ends of the housing to be delivered for use. The blades within the housing cause water in the air flow to condense inside the housing as air flows over the blades.

These and other objects of the invention are also fulfilled by a breathing assist device, comprising an air source, providing air, a tubing device, connected to the air source, a mask, connected to the tubing device and an adaptor. The adaptor is coupled between one of the air source and the tubing device or the tubing device and the mask. The adaptor comprises a housing, having two ends and a plurality of blades. The blades are disposed inside the housing and aligned in a direction of air flow. The path of air flow passing through both ends of the housing whereby air moving along the air flow path is delivered for use. The blades within the housing causing water in the air flow to condense inside the housing as air flows over the blades.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Example embodiments of the present invention will become more fully understood from the detailed description given herein below and the accompanying drawings, wherein like elements are represented by like reference numerals, which are given by way of illustration only and thus do not limit the example embodiments.

FIG. 1b is the top view of FIG. 1a;

DETAILED DESCRIPTION

The adaptor of the present invention is used in a breathing assist device to remove excess moisture from the air or gas delivered by the breathing assist device. Therefore, the adaptor can prevent unwanted water condensate in the tube or in the mask of a user.

Figure 1A:
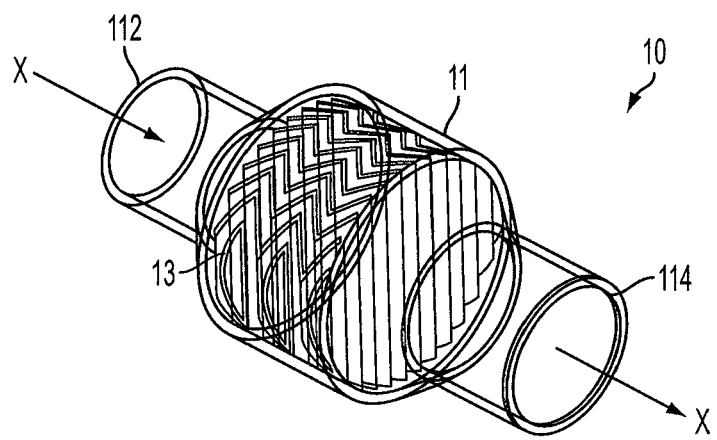
FIG. 1a illustrates a perspective view of one embodiment of the adaptor of the present invention.

FIG. 1a illustrates a perspective view of one embodiment of the adaptor of the present invention. Adaptor 10 of the present invention includes a housing 11 and a plurality of blades 13 disposed inside the housing 11. The housing in some of the figures including FIG. 1a is transparent for clarity in the explanation of the invention. This housing 11 can be transparent or non-transparent in use. The housing 11 and other components can be made from plastic, metal or any suitable material.

In this embodiment, the housing 11 has a cylindrical tubular shape and has two ends 112, 114. However the shapes of the housing should not limit the scope of invention. The housing can be in other shapes, such as rectangular tubular shape, triangular tubular shape, any other polygon tubular shape, spherical or any other desired shape. The two ends 112, 114 of the housing 11 define a path of air flow X as shown in FIG. 1a. Air flowing through the path X is delivered for use. The plurality of blades 13 are aligned in a direction of air flow X, which means the surface of each of the blades 13 is parallel to direction X. Air moves along the path of air flow X so that air also goes over the plurality of blades 13. While the present invention discusses movement of air through the invention, it is contemplated, that the devices can be used with medical gasses or any other desired gaseous media.

Figure 1B:
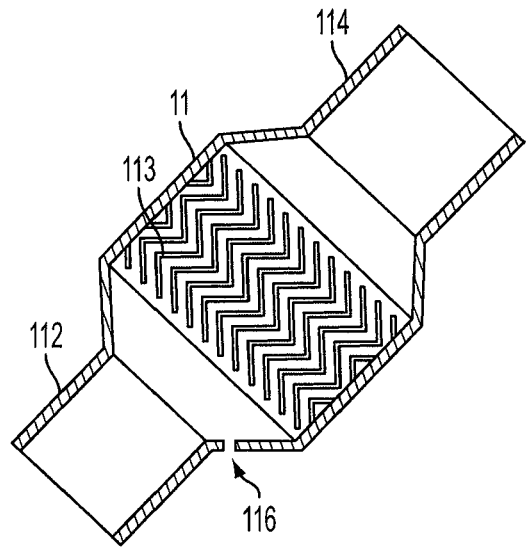

FIG. 1b is the top view of FIG. 1a. As shown in FIG. 1b, in this embodiment, the plurality of blades 13 are in zigzag shape, and each of the blades are juxtaposed to one another. In FIG. 1b, the blades 13 are uniformly positioned relative to one another. However, non-alignment of some or all of the blades is possible. It is merely necessary for the blades to permit air to flow through the housing. The zigzag shape of the blades is merely an exemplary embodiment. For example, the blades can be in chevron shape, flat shape, curved shape, wing shape or any other desired shape. The principle of blade shape design in the present invention is to facilitate water in air flowing through the blades to condense on the blades. When water vapor contacts with a surface at a temperature lower than the dew point under the humidity of the air, water in the air will start to condense on that surface. Therefore, the blade shape applied in the adaptor of the present invention provides sufficient contact surface area in order to remove excess water from the air. The water condenses on the blades inside the adaptor. This prevents condensation of water from the air flow path at a downstream point, such as within the tubing or a patient's mask as will be discussed later. While condensation of water is discussed, any gasified liquid in the air stream which might later condense can be caught by the adapter of the present invention.

Water condensed from the air passing through the housing of adaptor can be drained or stored in the housing 11 or in a separate container. Additionally, as seen in FIG. 1b, an outlet 116 can be formed on the housing 11 so that the water condensed inside the housing 11 will be drained outside the housing 11. In some embodiments, no outlet is formed on the housing and the water can be drained from one end of the housing to the ambient environment, a water collecting container or to another device.

Figure 2:
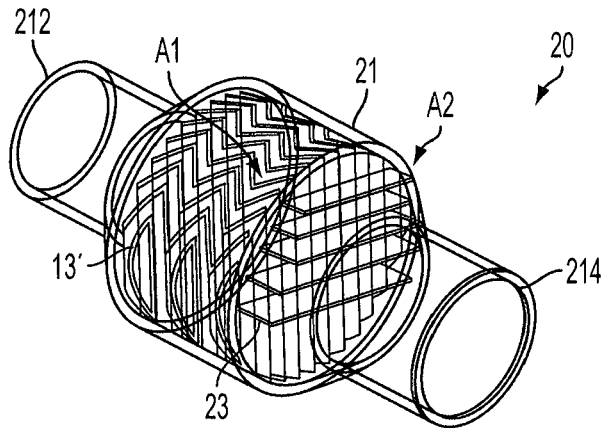
FIG. 2 is a perspective view of another embodiment of adaptor of the present invention.

FIG. 2 is a perspective view of another embodiment of the adaptor in the present invention. In this embodiment, the adaptor has a plurality of blades divided into two sets of blades. The housing 21 of the adaptor 20 accommodates these two sets of blades so that the first set of blades is disposed in a middle part of the housing 21 and the second set of blades 23 is disposed adjacent to the first set of blades 13' and close to one end 214 of housing 21. However, in other embodiments, the second set of blades 23 can be disposed at end 212 of the housing or two sets of blades 23 can be disposed at both two ends 212 and 214 of the housing 21.

In the embodiment of FIG. 2, the first set of blades 13' and the second set of blades 23 are different in shape. For example, in FIG. 2 the first set of blades 13' is in a zigzag shape while the second set of blades 23 is in flat shape. In other instances, the first set of blades can be in flat shape and the second set of blades can be in chevron, zigzag or wing-shape. Even more, the first set of blades and the second set of blades can be in the same shape, i.e., both in flat shape or both in zigzag shape, for example. In addition to flat and zigzag shapes, other shapes of blades can be applied in the present invention.

Moreover, while each set of blades is uniformly positioned relative to other blades in the set, other orientations of the blades within a set are possible. In the embodiment in FIG. 2, the alignments of the first set and the second set of blades are different. For example, in this embodiment, each surface of each of the first set of blades 13' has a first longitudinal axis A1 and each surface of each of the second set of blades 23 has a second longitudinal axis A2 which is perpendicular to the first longitudinal axis A1. However, in other embodiments of the present invention, the two longitudinal axes do not need to be perpendicular; these two axes may be set in any angle depending on design choice, or depending on the percentage of water in the air which is desired to be condensed.

Figure 3:
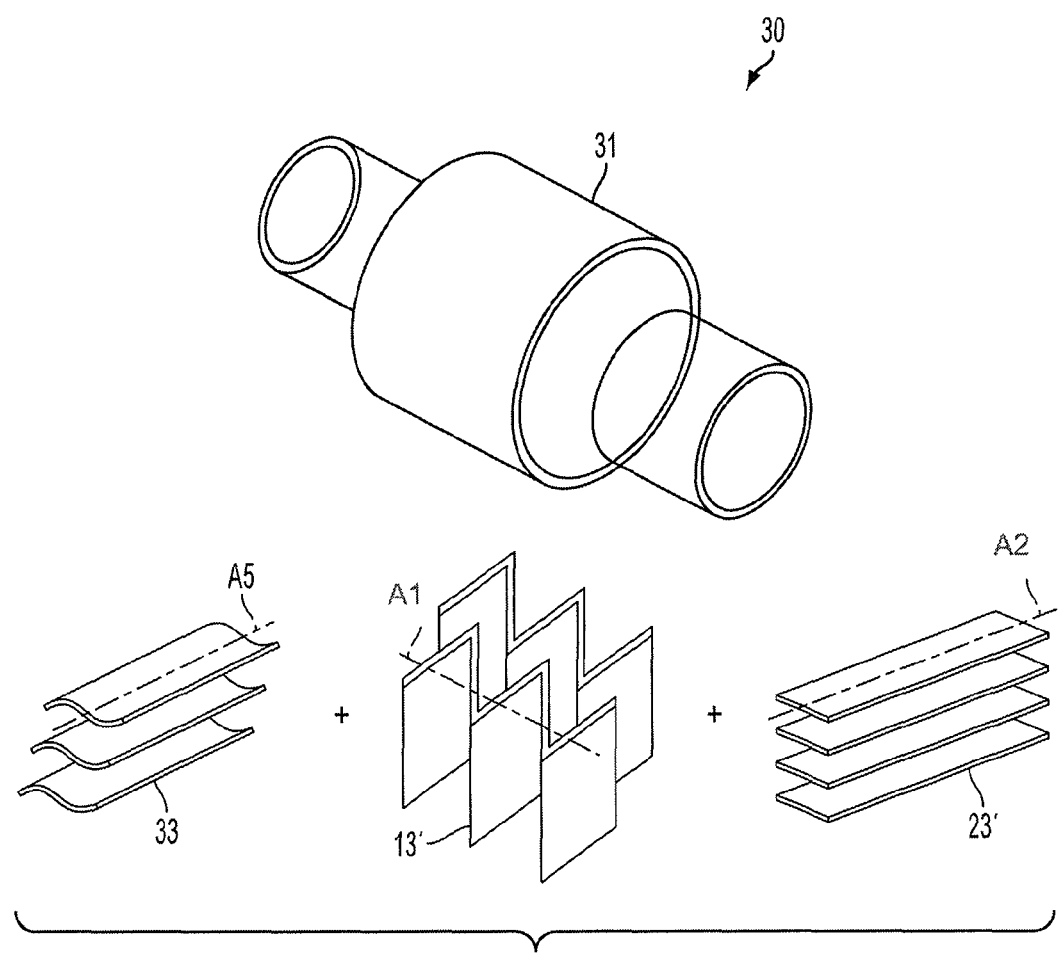
FIG. 3 illustrates an exploded view of another embodiment of adaptor of the present invention.

FIG. 3 illustrates an exploded view of another embodiment of adaptor in the present invention. As shown in FIG. 3, three sets of blades are applied in the adaptor 30. These three sets of blades included a first set of blades 13', a second set of blades 23' and a third set of blades 33. All of these blades are disposed inside the housing 31 and are aligned in a row along a path of air flow passing through the housing 31. In this embodiment the first set of blades 13' is in a zigzag shape, the second set of blades 23' is in a flat shape and the third set of blades 33 is in a curved shape. Please note that the shapes of the different sets of blades are not necessarily different; they can all be in the same shape such as zigzag or chevron shape; or two of the three sets can be in the same shape, for example, the second and the third sets of blades can be flat while the first set of blades can be zigzag shape. Still in another example, the first and the second set of blades can be zigzag while the third set of blades can be in a curved shape. Many different configurations of blades are possible. Moreover, the plurality of blades in the adaptor in other embodiments of the present invention can be divided into more than three sets of blades. For example, four or five sets of blades can be provided.

Similar to the embodiment shown in FIG. 2, in FIG. 3 one of the three sets of blades is disposed in a different alignment than other two sets of blades. More specifically, each surface of each of the first set of blades 13' is aligned along a first longitudinal axis A1 while each surface of each of the second set of blades 23' and each surface of each of the third set of blades 33 are respectively aligned along a second longitudinal axis A2 and a third longitudinal axis A5 which are both perpendicular to the first longitudinal axis A1. However, the angles among the longitudinal axes of the three sets of blades can vary and should not be limited by this description.

Figure 4:
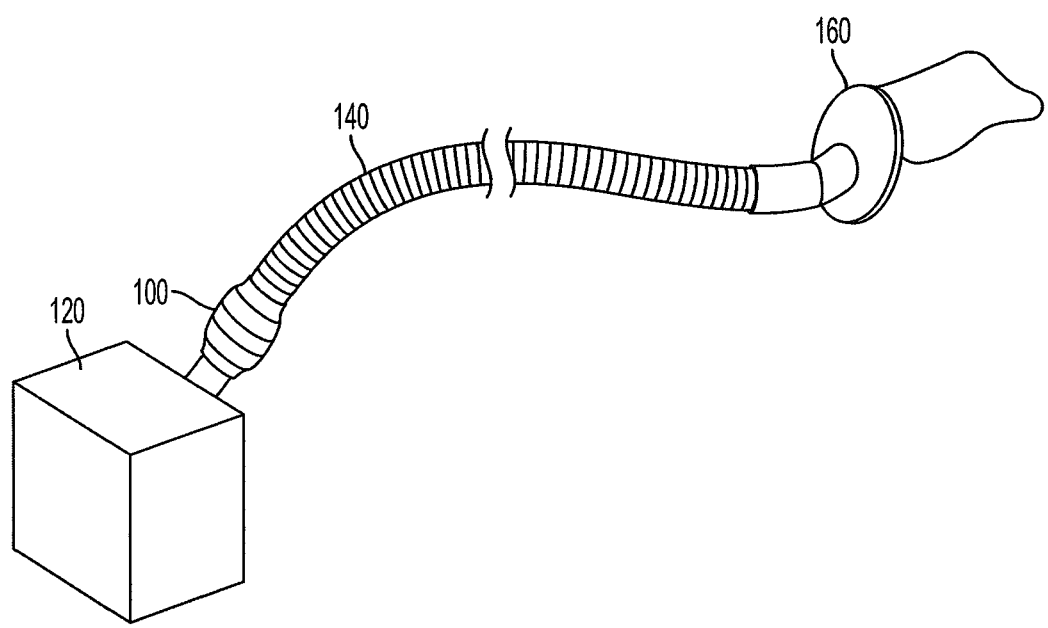
FIG. 4 shows a schematic view of one embodiment of a breathing assist device of the present invention.

The present invention further provides a breathing assist device utilizing the adaptor described above. FIG. 4 shows a schematic view of one embodiment of a breathing assist device in the present invention. The breathing assist device in this embodiment includes an adaptor 100, an air source 120, a tubing device 140 and a mask 160. The air source 120 provides air and the tubing device 140 is connected to the air source 120 for transmitting the air supplied from the air source 120. The mask 160 is connected to the tubing device 140 to receive the air and provide the air to a patient or user.

Different types of air sources known in the art can be used in the present invention. For example, a continuous positive airway pressure (CPAP) device is a common air source used for breathing assist device. It can be a continuous flow type or a demand flow type of air source; even more, it can either be an invasive type or a non-invasive type of air source. The type of air source may vary as desired and should not be limited by this description.

As shown in FIG. 4, in this embodiment the adaptor 100 is coupled between the air source 120 and the tubing device 140 so that air from the air source 120 will flow through the adaptor 100 before being sent to the user or patient. The adaptor 100 is contemplated as being readily detachable from the air source 120 and the tubing 140, but it could also be non-detachable mounted to either. Also, the adaptor in the breathing assist device in the present invention is not limited to be disposed between the air source and the tubing device; for example, the adaptor may be coupled between the tubing device and the mask in other embodiments. In short, the position of the adaptor in the breathing assist device in the present invention may vary and should not be limited by this description.

The detailed structure of the adaptor in this embodiment will not be repeated herein as it is already described above in the embodiments shown in FIG. 1 to FIG. 3. Please still note that the adaptor 100 in this embodiment defines a path of air flow (as shown by the arrow in FIG. 4). The air will pass through the two ends of the housing (please also refer to FIG. 1a) and move along the air flow path to be delivered through the tubing device 140 and the mask 160 for user by a patient. The adaptor disposed in the breathing assist device in the present invention facilitates condensation of excess water from the air inside the housing of the adaptor. Therefore, it will reduce the possibility of excessive water vapor in the air condensing inside the tubing or inside the mask. As a result, the breathing device utilizing the adaptor in the present invention will prevent a user/patient from choking because of rain-out effect. Other unwanted rain-out effects such as rattling of the tubing and pooling of water can be avoided.

The breathing assist device in this embodiment of the present invention further includes a humidifier installed inside the air source (not shown). The humidifier is used to maintain a desired humidity in the air supplied from the air source in order to provide a suitable breathe-in air for the user/patient. In other embodiments, a humidifier can be an independent element connected to the air source. Generally the humidifier is disposed between the air source and the mask so that air will be humidified before air is supplied to the user/patient. However, the breathing assist device can be without a humidifier if so desired.

In general, the adaptor disclosed in the present invention is disposed at a position angled to drain the condensed water from the housing. For instance, in FIG. 4 the adaptor 100 is disposed between the air source 120 and the tubing device 140 at an angle that water condensed in the housing can be drained from one end of the housing into the air source, for example 45°. Therefore, water can go into a water collection container of the humidifier for reuse as a source of humidity. In other embodiments, similar to the example in FIG. 1b, the adaptor may have an outlet on the housing and therefore water can be drained outside the breathing assist device through that outlet. Furthermore, in one embodiment, the adaptor in the present invention can be located in the humidifier itself. The scope of invention should not be limited by the position of the adaptor described above.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. An adaptor, used in a breathing assist device, the adaptor comprising:
   a housing, having two ends; and
   a plurality of condensation blades, disposed inside the housing and aligned in a first direction of air flow, a path of air flow passing through both ends of the housing in said first direction, whereby air moving along the path of air flow is delivered for use, the condensation blades extending completely across the housing so that all of the air flow is deviated from flowing in a straight line, water vapor in the path of air flow condenses on the condensation blades inside the housing as air flows over the condensation blades, and is collected for disposal;
   wherein the plurality of condensation blades are divided into a first set and a second set of condensation blades and each set is connected at ends thereof to the housing, the second set of condensation blades being disposed between the first set of condensation blades and at least one of the two ends of the housing, the first set of condensation blades having a different shape than the second set of condensation blades, each set having multiple condensation blades therein, space between the multiple condensation blades being empty, wherein the air flows between the multiple condensation blades of each set of condensation blades,
   wherein said first set of condensation blades has a longitudinal direction in said first direction, a transverse direction in a second direction perpendicular to the first direction, and has deviations in a third direction perpendicular to both the first and second directions; and wherein the second set of condensation blades has a longitudinal direction in the third direction and a transverse direction in the first direction.

2. The adaptor in claim 1, wherein the plurality of condensation blades are shaped to facilitate water vapor in the air flow to condense on the condensation blades.

3. The adaptor in claim 2, wherein the plurality of condensation blades are in a chevron, zigzag or flat shape.

4. The adaptor in claim 1, wherein the first set of condensation blades are chevron or zigzag and the second set of condensation blades are flat.

5. The adaptor in claim 1, wherein the first set of condensation blades and the second set of condensation blades are aligned in different directions.

6. The adaptor in claim 1, wherein a surface of each condensation blade of the first set of condensation blades has a first longitudinal axis and a surface of each condensation blade of the second set of condensation blades has a second longitudinal axis, the first longitudinal axis being perpendicular to the second longitudinal axis.

7. The adaptor in claim 1, wherein the first set of condensation blades are juxtaposed to one another and the second set of condensation blades are juxtaposed to one another.

8. The adaptor in claim 1, wherein the housing further has an outlet to drain the collected condensed water.

9. The adaptor in claim 1, wherein the housing is tubular.

10. The adaptor in claim 1, wherein the housing only has two openings to provide for air flow.

11. The adaptor in claim 1, wherein the plurality of condensation blades is divided into multiple sets of condensation blades, at least two of the multiple sets of condensation blades have different shapes.

12. The adaptor in claim 1, wherein the plurality of condensation blades are divided into a first set, a second set and a third set of condensation blades, wherein the first set of condensation blades is disposed between the second set and the third set of condensation blades, and the second set and the third set of condensation blades are disposed near the two ends of the housing respectively.

13. The adaptor in claim 12, wherein the shape of each of the first set of condensation blades, the shape of each of the second set of condensation blades and the shape of each of the third set of the condensation blades are different.

14. The adaptor in claim 12, wherein the first set of condensation blades are in chevron or zigzag shape, and the second set and the third set of condensation blades are in flat shape.

15. A breathing assist device, comprising:
an air source, providing air;
a tubing device, connected to the air source;
a mask, connected to the tubing device; and an adaptor, being coupled between one of the air source and the tubing device or the tubing device and the mask, the adaptor comprising:
a housing, having two ends; and
a plurality of condensation blades, disposed inside the housing and aligned in a first direction of air flow, a path of air flow passing through both ends of the housing in said first direction whereby air moving along the path of air flow is delivered for use, the condensation blades extending completely across the housing so that all of the air flow is deviated from flowing in a straight line, water vapor in the path of air flow condenses on the condensation blades inside the housing as air flows over the condensation blades, and is collected for disposal;
wherein the plurality of condensation blades are divided into a first set and a second set of condensation blades and each set is connected at ends thereof to the housing, the second set of condensation blades being disposed between the first set of condensation blades and at least one of the two ends of the housing, the first set of condensation blades having a different shape than the second set of condensation blades, each set having multiple condensation blades therein, space between the condensation blades being empty, wherein the air flows between the condensation blades of each set of condensation blades,
wherein said first set of condensation blades has a longitudinal direction in said first direction, a transverse direction in a second direction perpendicular to the first direction, and has deviations in a third direction perpendicular to both the first and second directions; and
wherein the second set of condensation blades has a longitudinal direction in the third direction and a transverse direction in the first direction.

16. The breathing assist device in claim 15, wherein the housing of the adaptor further has an outlet, the adaptor is disposed at a position angled to drain the collected condensed water from the outlet.

17. The breathing assist device in claim 15, further comprising a humidifier, connected between the air source and the tubing device, wherein the adaptor is disposed as part of the humidifier.

18. The breathing assist device in claim 15, wherein the plurality of condensation blades of the adaptor are shaped to cause water vapor in air flow to condense on the condensation blades.

19. The breathing assist device in claim 15, wherein the plurality of condensation blades are in a chevron, zigzag or flat shape.

* * * * *